United States Patent [19]
Yuen

[11] Patent Number: 5,932,573
[45] Date of Patent: Aug. 3, 1999

[54] SUBSTITUTED QUINOLINES AND ISOQUINOLINES AS CALCIUM CHANNEL BLOCKERS, THEIR PREPARATION AND THE USE THEREOF

[75] Inventor: Po-Wai Yuen, Ann Arbor, Mich.

[73] Assignee: Warner-Lambert Company, Morris Plains, N.J.

[21] Appl. No.: 09/040,177

[22] Filed: Mar. 17, 1998

Related U.S. Application Data

[62] Division of application No. 08/698,010, Aug. 13, 1996, Pat. No. 5,767,129
[60] Provisional application No. 60/002,723, Aug. 24, 1995, abandoned.

[51] Int. Cl.[6] .................... A61K 31/535; C07D 498/00
[52] U.S. Cl. ............................ 514/229.8; 544/95
[58] Field of Search ............................ 544/95; 514/229.8

[56] References Cited

FOREIGN PATENT DOCUMENTS 0556060  8/1993  European Pat. Off. .
55-072168  11/1978  Japan .

OTHER PUBLICATIONS

Bowersox, et al., "Neuronal Voltage–Sensitive Calcium Channels", *Drug News and Perspective*, 7(5):261–268 (1994).
Yamada, et al., Chemical Abstract 96:85389p.
Shterev and Kaneti, Chemical Abstract 108:142832v.
Bourquin, et al., "Synthese von Estern halogenierter Chinaldine und Chinoline", *Archiv der Pharmazie*, 295(5):383–400 (1962).
Brack, "Antimikrobielle Wirkung von 8–Hydroxychinolin–Derivaten, besonders von einigen neuen Estern", *Arzneimittel–Forsch.* 12, 133–144 (1962).

*Primary Examiner*—Mukund J. Shah
*Assistant Examiner*—Bruck Kifle
*Attorney, Agent, or Firm*—Elizabeth M. Anderson

[57] ABSTRACT

The present invention relates to novel substituted quinolines and isoquinolines and derivatives thereof useful in the treatment of neurological disorders. Methods of preparing the compounds, intermediates useful in the preparation and pharmaceutical compositions containing the compounds are also included. The compounds are useful in treating pain, cerebral ischemia, and other cerebrovascular disorders.

3 Claims, No Drawings

SUBSTITUTED QUINOLINES AND ISOQUINOLINES AS CALCIUM CHANNEL BLOCKERS, THEIR PREPARATION AND THE USE THEREOF

This application is a divisional of application Ser. No. 08/698,010 filed Aug. 13, 1996, now U.S. Pat. No. 5,767, 129 allowed, which claims the benefit of Provisional Application Ser. No. 60/002,723 filed Aug. 24, 1995, now abandoned.

BACKGROUND OF THE INVENTION

The present invention relates to novel substituted quinolines and isoquinolines thereof useful as pharmaceutical agents, to methods of their production, compositions which include these compounds and a pharmaceutically acceptable carrier, and to pharmaceutical methods of treatment. The novel compounds of the present invention are useful in the treatment of neurological disorders such as traumatic brain injury, cerebral ischemia, stroke, migraine, acute and chronic pain, epilepsy, Parkinson's disease, Alzheimer's disease, amyotrophic lateral sclerosis, multiple sclerosis, and depression. The compounds may also be useful for the treatment of nonneurological disorders such as asthma.

The entry of excessive amounts of calcium ion into neurons following an ischemic episode or other neuronal trauma has been well documented. Uncontrolled high concentrations of calcium in neurons initiates a cascade of biochemical events that disrupt normal cellular processes. Among these events are the activation of proteases and lipases, breakdown of neuronal membranes and the formation of free radicals which may ultimately lead to cell death. In particular, the selective N-type calcium channel blocker, SNX-111, has demonstrated activity in a number of models of ischemia and pain (Bowersox S. S., et al., *Drug News and Perspective*, 1994;7:261–268 and references cited therein).

Therefore, compounds which block N-type calcium channels may be useful in the treatment of neurological disorders such as traumatic brain injury, stroke, migraine, acute and chronic pain, epilepsy, Parkinson's disease, Alzheimer's disease, amyotrophic lateral sclerosis, multiple sclerosis, and depression.

SUMMARY OF THE INVENTION

The compounds of formula

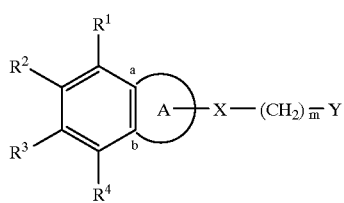

wherein $R^1$ to $R^4$, A, X, m, and Y are as defined below. The compounds are useful in treating various neurological disorders and nonneurological disorders such as asthma.

Other aspects of the invention include pharmaceutical compositions containing one or more compounds of Formula I and pharmaceutical compositions containing a therapeutically effective amount of a compound of the invention.

Other aspects of the instant invention are methods of treating neurological disorders such as: traumatic brain injury, cerebral ischemia, acute and chronic pain, epilepsy, Parkinsonism, Alzheimer's disease, amyotrophic lateral sclerosis, multiple sclerosis, and depression. Other disorders such as asthma are also treated.

DETAILED DESCRIPTION

The compounds of the instant invention are neuroprotective agents for use in cases where excess neuronal calcium accumulation contributes to cell death: stroke, cerebral ischemia resulting from cardiac arrest, head trauma, closed head injury, pain, amyotrophic lateral sclerosis, and also asthma.

The compounds of the instant invention are those of Formula I

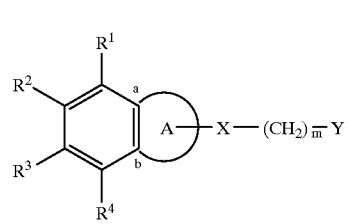

or a pharmaceutically acceptable salt thereof wherein:

$R^1$ and $R^2$ are each independently $OR^5$ or $CR^6R^7NR^8R^9$ and $R^1$ and $R^2$ cannot be the same;

$R^1$ and $R^2$ may be taken together with the ring to which they are attached to form a ring $-CR^6R^7NR^8CR^{10}R^{11}O-$ or $-OCR^{10}R^{11}NR^8CR^6R^7-$;

$R^3$ and $R^4$ are each independently hydrogen, alkyl, halogen, hydroxy, alkoxy, nitro, —NHCOalkyl, —NHCOaryl, or —NHCOalkylaryl;

A is a ring fused to the benzo ring at the positions a and b and formed by
a-NR—$(CR^{12}R^{13})_3$-b,
a-$CR^{12}R^{13}$—NR—$(CR^{12}R^{13})_2$-b,
a-$(CR^{12}R^{13})_2$—NR—$CR^{12}R^{13}$-b, and
a-$(CR^{12}R^{13})_3$—NR-b;

X is —$(CH_2)_n$— or —C=O;
m is an integer of from 0 to 9;
Y is $NR^{14}R^{15}$, —$CR^{16}R^{17}R^{18}$,

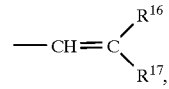

aryl, or heteroaryl;

$R^5$–$R^{11}$ and $R^{19}$ are each independently hydrogen, alkyl, aryl, or arylalkyl; or $R^8$ and $R^9$ are taken together with the nitrogen to which they are attached to form a ring of from 4 to 8 carbons, —$CH_2CH_2OCH_2CH_2$—, —$CH_2CH_2SCH_2CH_2$—, or —$CH_2CH_2R^{19}CH_2CH_2$—;

R is attached to the nitrogen in the A ring and is —X—$(CH_2)_m$—Y;

each $R^{12}$ and $R^{13}$ are each independently hydrogen, alkyl, and aryl;

n is an integer of from 0 to 1;

$R^{14}$ and $R^{15}$ are each independently hydrogen, alkyl, aryl, arylalkyl, heteroaryl, or heteroarylalkyl;

$R^{16}$ and $R^{17}$ are each independently selected from hydrogen, alkyl, aryl, arylalkyl, heteroaryl, and heteroarylalkyl; and R[18] is hydrogen, hydroxy, alkyl, aryl, arylalkyl, heteroaryl, and heteroarylalkyl.

Preferred compounds of the instant invention are those of Formula I wherein:

$R^1$ and $R^2$ are each independently —$OR^5$ or —$CR^6R^7NR^8R^9$;

$R^3$ and $R^4$ are each independently hydrogen, halogen, nitro, or alkyl;

A is a-$(CR^{12}R^{13})_2$—NR—$CR^{12}R^{13}$-b or a-$(CR^{12}R^{13})_3$—NR-b;

X is —$(CH_2)_n$ or —C=O;

m is an integer of from 3 to 5;

Y is —$CR^{16}R^{17}R^{18}$ or

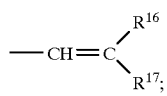

$R^5$–$R^{11}$ and $R^{19}$ are each independently hydrogen or alkyl;

$R^8$ and $R^9$ are taken together with the nitrogen to which they are attached to form a ring of from 4 to 8 carbons, —$CH_2CH_2OCH_2CH_2$, —$CH_2CH_2SCH_2CH_2$—, or —$CH_2CH_2R^{19}CH_2CH_2$—;

R is —X—$(CH_2)_m$—Y;

each $R^{12}$ and $R^{13}$ are each independently hydrogen or alkyl;

n is an integer of from 0 to 1;

$R^{16}$ and $R^{17}$ are each independently hydrogen, or aryl; and $R^{18}$ is hydrogen, hydroxy, or aryl.

Other preferred compounds are those of Formula I wherein:

$R^1$ and $R^2$ are taken together with the ring to which they are attached to form a ring —$CR^6R^7NR^8CR^{10}R^{11}O$— or —$OCR^{10}R^{11}NR^8CR^6R^7$—;

$R^3$ and $R^4$ are each independently hydrogen, halogen, nitro, or alkyl;

A is a-$(CR^{12}R^{13})_2$—NR—$CR^{12}R^{13}$-b or a-$(CR^{12}R^{13})_3$—NR-b;

X is —$(CH_2)_n$—or —C=O;

m is an integer of from 3 to 5;

Y is —$CR^{16}R^{17}R^{18}$ or

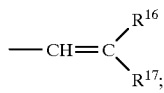

$R^5$–$R^{11}$ and $R^{19}$ are each independently hydrogen or alkyl;

R is —X—$(CH_2)_m$—Y;

each $R^{12}$ and $R^{13}$ are each independently hydrogen or alkyl;

n is an integer of from 0 to 1;

$R^{16}$ and $R^{17}$ are each independently hydrogen, or aryl; and $R^{18}$ is hydrogen, hydroxy, or aryl.

The most preferred compounds of the invention are:

6-Azepan-1-ylmethyl-2-(4,4-diphenylbutyl)-1,2,3,4-tetrahydroisoquinolin-5-ol;

6-Cyclohexylaminomethyl-2-(4,4-diphenylbutyl)-1,2,3,4-tetrahydroisoquinolin-5-ol;

6-Azepan-1-ylmethyl-2-[4,4-bis-(4-fluorophenyl)-butyl]-1,2,3,4-tetrahydroisoquinolin-5-ol;

6-Azepan-1-ylmethyl-1-(4,4-diphenylbutyl)-1,2,3,4-tetrahydroquinolin-5-ol;

6-Azepan-1-ylmethyl-2-(5,5-diphenylpentyl)-1,2,3,4-tetrahydroisoquinolin-5-ol;

6-Azepan-1-ylmethyl-2-(6,6-diphenylhex-5-enyl)-1,2,3,4-tetrahydroisoquinolin-5-ol;

6-Azepan-1-ylmethyl-2-(4,4-diphenylpropyl-1,2,3,4-tetrahydroisoquinolin-5-ol;

6-Azepan-1-ylmethyl-2-(6,6-diphenylhexyl)-1,2,3,4-tetrahydroisoquinolin-5-ol;

6-Azepan-1-ylmethyl-2-(4-phenylbutyl)-1,2,3,4-tetrahydroisoquinolin-5-ol,

6-Azepan-1-ylmethyl-2-[4-(4-bromophenyl)butyl]-1,2,3,4-tetrahydroisoquinolin-5-ol;

6-Azepan-1-ylmethyl-2-[4-(4-fluorophenyl)butyl]-1,2,3,4-tetrahydroisoquinolin-5-ol;

2-Cyclohexyl-7-(4,4-diphenylbutyl)-2,3,5,6,7,8-hexahydro-1H-4-oxa-2,7-diazaphenanthrene; and 2-Cyclohexyl-7-[4,4-bis-(4-fluorophenyl)butyl]-2,3,5,6,7,8-hexahydro-1H-4-oxa-2,7-diazaphenanthrene.

In the compounds of the present invention, the term alkyl, in general and unless specifically limited, means a straight, branched, or cyclic alkyl group of from 1 to 8 carbon atoms including but not limited to methyl, ethyl, propyl, isopropyl, butyl, isobutyl, cyclopentyl, and cyclohexyl.

Alkoxy is as defined above in alkyl but attached via an oxygen.

Aryl refers to a mono- or bicyclic carbocyclic aromatic ring, for example, but not limited to, phenyl and naphthyl. The aryl group may be unsubstituted or substituted by one or more substituents selected from alkyl, halogen, OH, $OCH_3$, $NO_2$, and NHCOalkyl, preferably $NHCOOCH_3$.

Heteroaryl is a mono- or polycyclic aromatic ring which contains a heteroatom, for example, but not limited to furanyl, thienyl, and isoquinolinyl.

Heteroarylalkyl is as above for alkyl and heteroaryl, for example, but not limited to 2-(2-thienyl)ethyl, 2-thienylmethyl, 2-pyridylmethyl, and the like.

Arylalkyl is defined as above in the terms alkyl and aryl as is, for example, and not limited to, benzyl, 2-phenylethyl, and 3-phenylpropyl is, for example, 4-phenylbutyl.

Carbocyclic ring is a 5- to 7-membered saturated or unsaturated ring and includes, for example, but not limited to, cyclopentane, cyclopentene, cyclohexane, cyclohexene, cycloheptane, cycloheptene, indane, and tetralin.

Halogen is fluorine, chlorine, bromine, or iodine; fluorine, chlorine, and bromine are preferred.

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono-, di-, and tricarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharma, Sci.*, 1977;66:1.

The acid addition salts of said basic compounds are prepared by contacting the free base form with a sufficient amount of the desired acid to produce the salt in the conventional manner. Preferably, a compound of Formula I can be converted to an acidic salt by treating with an aqueous solution of the desired acid, such that the resulting pH is less than four. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *J. of Pharma. Sci.*, 1977;66:1.

The base addition salts of said acidic compounds are prepared by contacting the free acid form with a sufficient amount of the desired base to produce the salt in the conventional manner. Preferably, a compound of Formula I can be converted to a base salt by treating with an aqueous solution of the desired base, such that the resulting pH is greater than nine. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all enantiomeric and epimeric forms as well as the appropriate mixtures thereof.

BIOLOGICAL ACTIVITY

The compounds of the invention exhibit valuable biological properties because of their ability to potently block calcium flux through N-type voltage-gated calcium channels. To measure interaction at the N-type $Ca^{2+}$ channel and calcium flux inhibition, the effects of the calcium channel blockers were measured in the assays described below.

Chick Whole-Brain Synaptosomal $^{45}$Calcium Flux Assay

Chicken brain synaptosomes contain voltage sensitive calcium channels which are inhibited by nanomolar concentrations of ω-contoxins and are therefore considered to be primarily N-type (Lundy P. M., Hamilton M. G., Frew R., *Brain Res.*, 1994;643:204–210). $^{45}$Ca flux into the synaptosomes may be induced by stimulation of the synaptosomal membrane with elevated potassium concentrations. A compound is assessed at various concentrations for its ability to inhibit this potassium stimulated calcium influx.

Methods

One- to five-week old chicks were killed by decapitation and whole brain was removed. The brainstem was discarded, and the remaining brain tissue was placed in ice-cold sucrose buffer (composition: 320 mM sucrose, 5.0 mM TRIS base, 0.1 mM EDTA, pH adjusted to 7.3 with HCl). The total wet weight of pooled brain tissue was determined, and the tissue was homogenized in 10 mL sucrose buffer per gram wet weight. A Potter S-type homogenizer (B. Braun Co.) with a glass tube and teflon pestle was used. Five strokes at 500 rpm were followed by four strokes at 800 rpm. The homogenate was poured into cold centrifuge tubes and centrifuged for 10 minutes at 3000 rpm (1,075 g) in a refrigerated 4° C. RC-5 centrifuge (Sorvall) using an SS-34 rotor. The supernatant was collected and centrifuged at 11,500 rpm (15,800 g) for 10 minutes The supernatant was discarded, and the pellet was resuspended in 1 mL sucrose buffer. Cold incubation buffer (composition: 1.2 MM $MgCl_2$, 22 mM HEPES, 11 mM glucose, 3 mM KCl, 136 mM choline chloride, pH adjusted to 7.3 with TRIS base) was added slowly to the suspension for a total volume of 30–40 mL. This mixture was centrifuged at 7,000 rpm (5,856 g) for 5 minutes. The supernatant was discarded, and the pellet was resuspended in 5 mL of incubation buffer per gram of original wet weight of brain. This synaptosomal suspension was kept on ice until the start of the assay, at which time 25 μL of synaptosome suspension were added to each well of a 96-well filter plate (Millipore) which contained 75 μL incubation buffer with or without drug. Drugs were dissolved in DMSO or $H_2O$, and the concentration of DMSO was less than or equal to 1%.

Synaptosomes were pre-incubated in the presence or absence of drug for 5 minutes at room temperature before the addition of radioactive calcium. Drugs were present throughout the assay. Two μCi/mL stocks of $^{45}CaCl_2$ were prepared in basal buffer (composition: incubation buffer plus 1 mM $CaCl_2$) and in stimulation buffer (composition: 1.2 mM $MgCl_2$, 22 mM HEPES, 11 mM glucose, 37 mM KCl, 102 mM choline chloride, 1 mM $CaCl_2$, pH adjusted to 7.3 with TRIS base). One hundred microliter of radioactive basal or stimulation buffer were pipetted into a pre-incubated plate of synaptosomes, using a Quadra 96 pipetter (Tomtec). The final KCl concentration was 3 mM for the basal condition and 20 mM for the stimulated condition; the final $CaCl_2$ concentration was 0.5 mM with 1 μCi/mL of $^{45}CaCl_2$. The plate was filtered under vacuum after a 30-second incubation with radioactivity. The filters were washed twice with 200 μL of wash buffer (composition: 140 mM choline chloride, 3 mM EGTA, 22 mM HEPES, pH adjusted to 7.3 with TRIS base). Plates were allowed to dry completely. Scintillation fluid was added (20 μL/well), and the plates were counted in a Wallace Microbeta plate counter. Basal $^{45}CaCl_2$ flux (3 mM KCl) was subtracted from stimulated $^{45}CaCl_2$ flux (20 mM KCl) in both control and drug-treated conditions, and data were expressed as percent inhibition of the adjusted control response. Values obtained in this way were plotted as a function of drug concentration and $IC_{50}$ values were calculated.

Measurement of N-type Ca2+ Channel Blocking Potencies of Compounds in IMR-32 Cells Using the Fluorescent Ca2+ Indicator Indo-1

IMR-32 cells are a human tumoral cell line of neural origin. The IMR-32 cell line has been shown to contain both N- and L-type voltage sensitive calcium channels. Calcium flux into these cells may be induced by stimulation with elevated potassium concentrations. The L-channel component of calcium flux may be blocked by adding 5 $\mu$M nitrendipine. The remaining component of calcium entry into the IMR-32 cells is due to calcium flux through N-type calcium channels. Intracellular calcium concentrations are measured using the fluorescent calcium indicator Indo-1. The effect of drug concentration on calcium uptake is studied.

Methods

The IMR-32 cell line was obtained from the American Type Culture Collection (Rockville, Md.).

Cells were grown in Eagle's Minimum Essential Medium with Earle's salts supplemented with 10% fetal bovine serum, 2 mM L-Gln and antibiotic/antimicotic mixture (Gibco). At approximately 80% confluency, differentiation was induced by the addition of 1 mM dibutyryl cAMP and 2.5 $\mu$M bromodeoxyuridine to the medium. After 7 to 13 days of differentiation, cells were detached using 0.5 mM EDTA and loaded with five 5 $\mu$M Indo-1 acetoxymethyl ester (Molecular Probes, Eugene, OR) at 30° C. for 45 minutes. Loaded cells were washed twice, resuspended (~10$^7$ cells/mL) in assay buffer (10 MM HEPES/Tris pH 7.4 in Hank's Balanced Salt Solution without bicarbonate or phenol red containing 0.5% bovine serum albumin) and kept on ice until use. Fluorescence measurements were carried out in a Photon Technology International (PTI, South Brunswick, N.J.) Model RF-F3004 spectrofluorometer with dual emission monochromators using excitation at 350 nm and emission at 400 and 490 nm. The instrument was equipped with a thermostatted cuvette holder with stirring capabilities as well as with a computer-controlled pump which allowed for reagent addition during measurement. Instrument control and data collection was done by PTI's OSCAR software running on an IBM compatible computer. Different concentrations of the test compounds (60 $\mu$L in dimethyl sulfoxide) were added to 5.94 mL of assay buffer containing approximately 3×10$^6$ loaded cells, and 5 $\mu$M Nitrendipine (in 30 $\mu$L EtOH) to block L-type Ca$^{2+}$ channels. Samples were incubated for 10 minutes at 30° C. and then aliquoted into three 10×10 mm disposable acrylic cuvettes. Emission signals at 400 and 490 nm were acquired from each cuvette at 30° C. for 50 seconds. At 20 seconds after the start of reading, cells were depolarized by the addition of 160 $\mu$L of stimulation solution (1M KCl, 68 mM CaCl$_2$) to the cuvette via the computer-controlled pump. Ratio of dual emission signals (400 nm/490 nm), which is proportional to intracellular Ca$^{2+}$ concentration, was plotted against time, and the difference between maximal response after stimulation and basal value (before stimulation) was determined. Values obtained in this way were plotted as a function of drug concentration. IC$_{50}$ values of test compounds were calculated by fitting a four-parameter logistic function to the data using the least squares method.

TABLE 1

Inhibition of Calcium Flux in Chicken Synaptosomes and IMR-32 Cells

| Example | Inhibition of $^{45}$Ca$^{+2}$ Influx in Chick Synaptosomes IC$_{50}$ $\mu$M | Inhibition of Ca$^{+2}$ Influx in IMR-32 Cells IC$_{50}$ $\mu$M |
| --- | --- | --- |
| 6 | 0.49 | 0.82 |
| 7 | 3.7 | 1.0 |
| 8 | 3.4 | 1.1 |
| 11 | Not Tested | 1.3 |

Table 1 above summarizes the findings of the two assays. Based on these findings, the compounds of the invention are believed to be useful in treating calcium channel-related diseases.

The following nonlimiting examples illustrate the present invention.

EXAMPLE 1

1,1-Diphenyl-1,4-butanediol

4-Butyrolactone (11.93 mL, 0.155 mol) was dissolved in anhydrous THF and cooled to 0° C. Phenylmagnesium bromide (3 M in ether, 112 mL) was added dropwise over 30 minutes to the reaction under N$_2$. After the addition, the reaction was warmed to room temperature overnight. Additional phenylmagnesium bromide (3 M in ether, 103 mL) was added, and the reaction stirred at room temperature overnight. The reaction was quenched with saturated NH$_4$Cl (150 mL). Ether (200 mL) and 10% HCl (100 mL) were added. The organic layer was separated and washed with 10% HCl (100 mL), brine (100 mL), and then dried over MgSO$_4$. The solution was filtered, concentrated, and the crude material chromatographed on silica gel eluting with 50% EtOAc/Hexanes to give 26.94 g (72%) of desired product as an off-white solid.

$^1$H NMR (400 MHz, CDCl$_3$): δ 7.45–7.15 (m, 10H), 3.65 (t, 2H, J=5.9 Hz), 2.42 (m, 4H), 1.57 (m, 2H).

EXAMPLE 2

4,4-Diphenyl-1-butanol 1,1-Diphenyl-1,4-butanediol (26.62 g, 0.110 mol) was dissolved in MeOH and shaken with 20% Pd/C (1.50 g) on a Parr apparatus under an H$_2$ atmosphere (50 psi) for 17 hours. The MeOH was removed in vacuo, and the residue chromatographed on silica gel eluting with 35% EtOAc/Hexanes gave 22.53 g (91%) of desired product.

$^1$H NMR (400 MHz, CDCl$_3$)z 6 7.3–7.1 (m, 10H), 3.90 (t, 1H, J=7.9 Hz), 3.63 (t, 2H, J=6.5 Hz), 2.1 (q, 2H, J=7.9 Hz), 1.5 (m, 2H).

EXAMPLE 3

1-Bromo-4,4-diphenylbutane 4,4-Diphenyl-1-butanol (22.41 g, 0.099 mol) was dissolved in ether (250 mL). CBr$_4$ (41.07 g, 0.123 mol) was added and the reaction cooled to 0° C. Triphenylphosphine (38.96 g, 0.148 mol) in ether (400 mL) was added dropwise to the reaction. The reaction was then allowed to warm to room temperature overnight. DMSO (3.51 mL) was added, and the reaction allowed to stir for 8 hours. The white precipitate was filtered and washed with ether (100 mL). The ether was removed in vacuo, and the residue washed with hexanes and filter. The hexanes were removed in vacuo, and the residue chromatographed on silica gel eluting with hexanes to give 20.72 g (72%) of desired product as an oil.

$^1$H NMR (200 MHz, CDCl$_3$): δ 7.4–7.1 (m, 10H), 3.92 (t, 1H, J=7.5 Hz), 3.41 (t, 2H, J=6.5 Hz), 2.35–2.1 (m, 2H), 1.95–1.75 (m, 2H).

EXAMPLE 4

2-(4,4-Diphenylbutyl)-5-hydroxyisoguinolinium bromide

A mixture of 5-hydroxyisoquinoline (2.17 g, 14.95 mmol) and 1-bromo-4,4-diphenylbutane (4.79 g, 16.56 mmol) in 75 mL of anhydrous DMF was stirred at 80° C. for 16 hours. The reaction mixture was cooled to room temperature. Ethyl acetate (200 mL) was added to precipitate product. The solid was collected by filtration and washed with ethyl acetate (1×70 mL). The solid was air-dried to give 4.52 g of product as an off-white solid.

$^1$H NMR (300 MHz, DMSO-d$_6$): δ 11.48 (s, 1H), 9.99 (s, 1H), 8.59 (ABq, 2H, J$_{AB}$=6.85 Hz, υ$_{AB}$=35.99 Hz), 7,88 (d, 2H, J=4.58 Hz), 7.54 (m, 1H), 7.28 (m, 8H), 7.17 (m, 2H), 4.73 (t, 2H, J=6.87 Hz), 3.98 (t, 1H, J=7.75 Hz), 2.11–2.06 (m, 2H), 1.95–1.90 (m, 2H).

EXAMPLE 5

2-(4,4-Diphenylbutyl)-1,2,3,4-tetrahydroisoguinolin-5-ol

To a solution of 2-(4,4-diphenylbutyl)-5-hydroxyisoquinolinium bromide (2.29 g, 5.27 mmol) in 100 mL of methanol was added 20% Pd/C catalyst (0.7 g). The reaction mixture was shaken under 50 psi of hydrogen at room temperature for 18 hours. The catalyst was then removed by filtration through a pad of Celite. The residue was washed with methanol, and the filtrate was concentrated under vacuum. The white solid obtained was neutralized with saturated sodium bicarbonate solution. The mixture was extracted with ethyl acetate (2×200 mL). The organic extracts were collected and dried with magnesium sulphate, filtered and concentrated to give 1.9 g of crude product as a yellow oil.

$^1$H NMR (300 MHz, CDCl$_3$): δ 7.31–7.15 (m, 10H), 6.93 (t, 1H, J=7.87 Hz), 6.56 (d, 1H, J=7.63 Hz), 6.46 (d, 1H, J=7.63 Hz), 3.93 (t, 1H, J=7.93 Hz), 3.56 (s, 2H), 2.54 (m, 2H), 2.11 (m, 2H), 1.61 (m, 2H)

EXAMPLE 6

6-Azepan-1-ylmethyl-2-(4,4-diphenylbutyl)-1,2,3,4-tetrahydroisoquinolin-5-ol

To a solution of 2-(4,4-diphenylbutyl)-1,2,3,4-tetrahydro-isoquinolin-5-ol (1.9 g, 5.32 mmol) in 5 mL of absolute ethanol was added hexamethyleneimine (0.6 mL, 5.32 mmol) followed by a 37% formaldehyde solution (0.4 mL, 5.34 mmol). The reaction mixture was stirred at room temperature for 4 days. Ethyl acetate (60 mL) and half saturated sodium chloride solution (60 mL) were added. The organic layer was collected, and the aqueous layer was extracted with ethyl acetate (2×30 mL). The combined organic extracts was dried with magnesium sulphate, filtered, and concentrated to give a brown oil The oil was chromatographed on silica gel eluted with 10% methanol in ethyl acetate to give 1.9 g of a yellow oil. The oil was dissolved in 30 mL of methanol. A solution of hydrogen chloride in ether (1.0 M, 9 mL) was added at room temperature to form a brown precipitate. The solid was collected by filtration and washed with 30% methanol in ether solution (2×60 mL) and then with ether (3×60 mL). The solid was air-dried overnight to give 1.79 g of a white solid as the dihydrochloride salt, mp=255–256° C.

Analysis Calculated for C$_{32}$H$_{42}$Cl$_2$N$_2$O: C, 70.97; H, 7.82; N, 5.17. Found: C, 70.45; H, 7.67, N, 5.09.

EXAMPLE 7

6-Cyclohexylaminomethyl-2-(4,4-diphenylbutyl)-1,2,3,4-tetrahydroisoguinolin-5-ol 2-(4,4-Diphenylbutyl)-1,2,3,4-tetrahydro-isoquinolin-5-ol (2.44 g, 6.83 mmol) was dissolved in EtOH (70 mL). Formaldehyde (37%, 0.536 mL, 7.17 mmol) and cyclohexylamine (0.820 mL, 7.17 mmol) were added, and the reaction heated to 50° C. for 10 days. The solvent was removed and the crude reaction chromatographed on silica gel eluting with EtOAc. Isolate 2.44 g (76 %) of product as an oil. The oil (0.61 g, 1.30 mmol) was then dissolved in Et$_2$O (10 mL). Oxalic acid (0.33 g, 2.62 mmol) in EtOH (1 mL) was added to the ether solution, and the reaction stirred at room temperature for 18 hours. The light tan precipitate was filtered and washed with EtOAc and dried in vacuo over P$_2$O$_5$ to give 0.61 g (73%) of the oxalic acid salt, mp=127–144° C.

Analysis calculated for C$_{32}$H$_{40}$N$_2$O.1.84 C$_2$H$_2$O$_4$: C, 67.56; H, 6.94; N, 4.42. Found: C, 67.56; H, 6.90; N, 4.26.

EXAMPLE 8

2-Cyclohexyl-7-(4,4-diphenylbutyl)-2,3,5,6,7,8-hexahydro-1H-4-oxa-2,7-diazaphenanthrene 6-Cyclohexylaminomethyl-2-(4,4-diphenylbutyl)-1,2,3,4-tetrahydro-isoquinolin-5-ol (1.84 g, 3.93 mmol) was dissolved in MeOH (35 mL). Formaldehyde (37%, 0.60 mL, 8.0 mmol) was added, and the reaction stirred at room temperature for 96 hours. The MeOH was removed in vacuo, and the crude material filtered through a plug of silica gel eluting with EtOAc to give 1.68 g (89%) of product as an oil. MS(CI with 1% NH$_3$ in CH$_4$) m/e 481 (M$^+$+1). The oil (1.68 g, 3.49 mmol) was then dissolved in ether (25 mL). Oxalic acid (0.88 g, 6.99 mmol) in EtOH (2 mL) was added to the ether solution, and more ether (10 mL) was added to break up solid precipitate. The reaction was stirred for 2 hours, the solid filtered and washed with EtOAc. Drying in vacuo yielded 1.83 g (79%) of the oxalic acid salt, mp=102–117° C.

Analysis calculated for C$_{33}$H$_{40}$N$_2$O.2.19 C$_2$H$_2$O$_4$: C, 66.23; H, 6.60; N, 4.13. Found: C, 66.24; H, 6.39; N, 3.89.

EXAMPLE 9

2-[4,4-Bis-(4-fluorophenyl)butyl]-5-hydroxyiso quinolinium bromide

A mixture of 5-hydroxyisoquinoline (4.56 g, 31.41 mmol) and 4,4-bis(4-fluorophenyl)butyl bromide (11.40 g, 35.06 mmol. Prepared according to the procedure of Miroslav Rajsner, et al., *Czech. Collect. Czech. Chem. Commun.*, 1978;43:1760) in 100 mL of anhydrous DMF was stirred at 80° C. overnight. The reaction mixture was cooled to 0° C. Ethyl acetate (400 mL) was added to precipitate product. The solid was collected by filtration and washed with ethyl acetate (2×100 mL). The solid was air-dried to give 10.74 g of product as an off-white solid.

¹H NMR (400 MHz, DMSO-d₆): δ 11.42 (br. s, 1H), 9.92 (s, 1H), 8.58 (d, 1H, J=7.08 Hz), 8.46 (d, 1H, J=6.84 Hz), 7.82 (d, 2H, J=4.64 Hz), 7.47 (t, 1H, J=4.40 Hz), 7.25 (m, 4H), 7.04 (m, 4H), 4.66 (t, 2H, J=7.08 Hz), 3.98 (m, 1H), 1.99 (m, 2H), 1.84 (m, 2H).

EXAMPLE 10

2-[4,4-Bis-(4-fluorophenyl)butyl]-1,2,3,4-tetrahydroisoquinolin-5-ol

To a solution of 2-[4,4-bis-(4-fluorophenyl)-butyl]-5-hydroxyisoquinolinium bromide (4.99 g, 10.61 mmol) in 165 mL of methanol at 0° C. was added sodium borohydride (1.54 g, 40.71 mmol). The reaction mixture was stirred at 0° C. for 15 minutes, then at room temperature for 15 minutes. The mixture was concentrated on a rotavap. The residue was dissolved in ethyl acetate (200 mL) and washed with saturated ammonium chloride solution (150 mL). The organic layer was collected, and the aqueous layer was extracted with ethyl acetate (1×100 mL). The combined organic layers was dried with magnesium sulphate, filtqred, and concentrated to give 1.9 g of crude product as a brown oil. The oil was chromatographed on silica gel eluted with 50% ethyl acetate in hexanes to give 2.54 g of product.

¹H NMR (400 MHz, CDCl₃): δ 7.14–7.10 (m, 4H), 6.97–6.89 (m, 5H), 6.56 (m, 2H), 3.85 (t, 1H, J=7.81 Hz), 3.48 (s, 2H), 2.66 (m, 4H), 2.47 (m, 2H), 2.02 (m, 2H), 1.50 (m, 2H).

EXAMPLE 11

6-Azepan-1-ylmethyl-2-[4,4-bis-(4-fluorophenyl)-butyl]-1,2,3,4-tetrahydroisoquinolin-5-ol To a solution of 2-[4,4-bis-(4-fluorophenyl)-butyl]-1,2,3,4-tetrahydroisoquinolin-5-ol (2.54 g, 6.46 mmol) in 40 mL of tetrahydrofuran was added hexamethyleneimine (1.2 mL, 10.65 mmol) followed by a 37% formaldehyde solution (0.8 mL, 10.67 mmol). The reaction mixture was stirred at room temperature overnight. Hexamethyleneimine (0.6 mL, 5.32 mmol) and a 37% formaldehyde solution (0.4 mL, 5.34 mmol) was added, and the reaction mixture was stirred at room temperature for 5 hours. After the 5-hour period, another portion of hexamethyleneimine (0.6 mL, 5.32 mmol) and a 37% formaldehyde solution (0.4 mL, 5.34 mmol) was added. The reaction mixture was stirred at room temperature overnight. The mixture was concentrated on a rotavap. The brown oil was washed with brine solution. The mixture was extracted with ethyl acetate (2×100 mL). The organic layer was collected and dried with magnesium sulphate, filtered, and concentrated. The oil was chromatographed on silica gel eluted first with 75% ethyl acetate in hexanes to remove the phenol starting material then with pure ethyl acetate to give 1.84 g of the product as an off-white solid. The solid was dissolved in 40 mL of methanol and 50 mL ethyl ether. A solution of hydrogen chloride in ether (1.0 M, 7.5 mL) was added at room temperature to precipitate out the product as its hydrochloride salt. The solid was collected by filtration and washed with ether (3×50 mL). The solid was air-dried overnight to give 1.95 g of a white solid as the dihydrochloride salt, mp=238–239° C. (dec).

Analysis calculated for C₃₂H₃₈F₂N₂O.2HCl: C, 66.54; H, 6.98; N, 4.85. Found: C, 66.32, H, 6.97, N, 4.78.

I claim:

1. A compound of formula

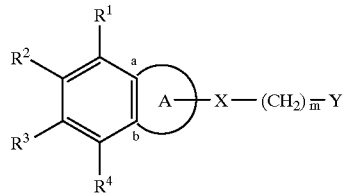

or a pharmaceutically acceptable salt thereof wherein:

$R^1$ and $R^2$ are taken together with the ring to which they are attached to form a ring —$CR^6R^7NR^8CR^{10}R^{11}O$— or —$OCR^{10}R^{11}NR^8CR^6R^7$—;

$R^3$ and $R^4$ are each independently hydrogen, alkyl, halogen, hydroxy, alkoxy, nitro, —NHCOalkyl, —NHCOaryl, or —NHCOalkylaryl;

A is a ring fused to the benzo ring at the positions a and b and formed by a-NR—$(CR^{12}R^{13})_3$-b, a-$CR^{12}R^{13}$—NR—$(CR^{12}R^{13})_2$-b, a-$(CR^{12}R^{13})_2$—NR—$CR^{12}R^{13}$-b, and a-$(CR^{12}R^{13})_3$—NR-b;

X is —$(CH_2)_n$— or —C=O, m is an integer of from 0 to 9;

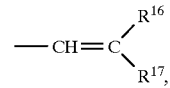

Y is $NR^{14}R^{15}$, —$CR^{16}R^{17}R^{18}$, aryl, or heteroaryl;

$R^5$–$R^{11}$ and $R^{19}$ are each independently hydrogen, alkyl, aryl, or arylalkyl; or R is attached to the nitrogen in the A ring and is —X—$(CH_2)_m$—Y;

each $R^{12}$ and $R^{13}$ are each independently hydrogen, alkyl, and aryl;

n is an integer of from 0 to 1;

$R^{14}$ and $R^{15}$ are each independently hydrogen, alkyl, aryl, arylalkyl, heteroaryl, or heteroarylaklyl;

$R^{16}$ and $R^{17}$ are each independently selected from hydrogen, alkyl, aryl, arylalkyl, heteroaryl, and heteroarylalkyl; and $R^{18}$ is hydrogen, hydroxy, alkyl, aryl, arylalkyl, heteroaryl, or heteroarylalkyl.

2. A compound according to claim 1 wherein $R^1$ and $R^2$ are taken together with the ring to which they are attached to form a ring —$CR^6R^7NR^8$ $CR^{10}R^{11}O$— or —$OCR^{10}R^{11}NR^8CR^6R^7$ —;

$R^3$ and $R^4$ are each independently hydrogen, halogen, nitro, or alkyl;

A is a-$(CR^{12}R^{13})_2$—NR—$CR^{12}R^{13}$-b or a-$(CR^{12}R^{13})_3$—NR-b;

X is —$(CH_2)_n$— or —C=O;

m is an integer of from 3 to 5;

Y is —$CR^{16}R^{17}R^{18}$ or

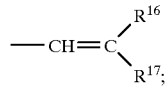

$R^5$–$R^{11}$ and $R^{19}$ are each independently hydrogen or alkyl;

R is —X—$(CH_2)_m$—Y;

each $R^{12}$ and $R^{13}$ are each independently hydrogen or alkyl;

n is an integer of from 0 to 1;

$R^{16}$ and $R^{17}$ are each independently hydrogen or aryl; and $R^{18}$ is hydrogen, hydroxy, or aryl.

3. A compound according to claim 1 selected from

2-Cyclohexyl-7-(4,4-diphenylbutyl)-2,3,5,6,7,8-hexahydro-1H-4-oxa-2,7-diazaphenanthrene, and 2-Cyclohexyl-7-[4,4-bis-(4-fluorophenyl)-butyl]-2,3,5,6,7,8-hexahydro-1H-4-oxa-2,7-diazaphenanthrene.

* * * * *

UNITED STATES PATENT AND TRADEMARK OFFICE
CERTIFICATE OF CORRECTION

PATENT NO. : 5,932,573
DATED : August 3, 1999
INVENTOR(S) : PO-Wai Yuen

It is certified that error appears in the above-identified patent and that said Letters Patent is hereby corrected as shown below:

Column 12, lines 39-40, remove "$-CH=C\begin{smallmatrix}R^{16}\\ \\ R^{17}\end{smallmatrix}$,".

Column 12, line 43, after "$-CR^{16}R^{17}R^{18}$,"

insert -- $-CH=C\begin{smallmatrix}R^{16}\\ \\ R^{17}\end{smallmatrix}$, --.

Signed and Sealed this

Eighteenth Day of April, 2000

Q. TODD DICKINSON

*Attest:*

*Attesting Officer*  *Director of Patents and Trademarks*